United States Patent
Yokobori et al.

(12)

(10) Patent No.: US 10,294,319 B2
(45) Date of Patent: May 21, 2019

(54) TRIACRYLATE COMPOUNDS AND METHODS FOR PRODUCING THE SAME, AND COMPOSITIONS

(71) Applicant: MITSUBISHI GAS CHEMICAL COMPANY, INC., Chiyoda-ku (JP)

(72) Inventors: Umi Yokobori, Niigata (JP); Taketo Ikeno, Niigata (JP); Hideyuki Sato, Niigata (JP); Ryuji Hasemi, Niigata (JP)

(73) Assignee: MITSUBISHI GAS CHEMICAL COMPANY, INC., Chiyoda-ku (JP)

( * ) Notice: Subject to any disclaimer, the term of this patent is extended or adjusted under 35 U.S.C. 154(b) by 33 days.

(21) Appl. No.: 15/521,142

(22) PCT Filed: Oct. 21, 2015

(86) PCT No.: PCT/JP2015/079735
§ 371 (c)(1),
(2) Date: Apr. 21, 2017

(87) PCT Pub. No.: WO2016/036919
PCT Pub. Date: Apr. 28, 2016

(65) Prior Publication Data
US 2017/0335043 A1    Nov. 23, 2017

(30) Foreign Application Priority Data

Oct. 22, 2014   (JP) .................. 2014-215803

(51) Int. Cl.
| C08F 22/26 | (2006.01) |
|---|---|
| C08F 265/06 | (2006.01) |
| C08F 22/10 | (2006.01) |
| C07C 67/03 | (2006.01) |
| C07C 67/08 | (2006.01) |
| C07C 69/54 | (2006.01) |
| C08F 20/20 | (2006.01) |
| C09D 11/101 | (2014.01) |
| C08F 10/00 | (2006.01) |
| C09J 4/00 | (2006.01) |
| C08F 290/06 | (2006.01) |
| C09D 4/00 | (2006.01) |
| C08F 120/12 | (2006.01) |
| G01R 33/46 | (2006.01) |

(52) U.S. Cl.
CPC ............ *C08F 265/06* (2013.01); *C07C 67/03* (2013.01); *C07C 67/08* (2013.01); *C07C 69/54* (2013.01); *C08F 10/00* (2013.01); *C08F 20/20* (2013.01); *C08F 22/10* (2013.01); *C08F 22/26* (2013.01); *C08F 290/067* (2013.01); *C09D 4/00* (2013.01); *C09D 11/101* (2013.01); *C09J 4/00* (2013.01); *C08F 120/12* (2013.01); *C08F 2810/20* (2013.01); *G01R 33/46* (2013.01)

(58) Field of Classification Search
CPC .......... C07C 67/03; C07C 67/08; C07C 69/54; C08F 22/10; C08F 22/26
See application file for complete search history.

(56) References Cited

FOREIGN PATENT DOCUMENTS

| JP | 55-85510 A | 6/1980 |
|---|---|---|
| JP | 59-86666 A | 5/1984 |
| JP | 61-1642 A | 1/1986 |
| JP | 2-261831 A | 10/1990 |
| JP | 6-271623 A | 9/1994 |
| JP | 2010-134073 A | 6/2010 |
| JP | 2012-144641 A | 8/2012 |
| WO | WO 2012/096330 A1 | 7/2012 |

OTHER PUBLICATIONS

International Search Report dated Jan. 26, 2016 in PCT/JP2015/079735 filed Oct. 21, 2015.
Kunihiro Ichimura, "Dai 5 sho (Chapter 5) Rajikaru jugokei monoma origoma (Radical polymerizable monomers and oligomers" UV kouka no kiso to jissen (Foundation and practice of UV curing), Oct. 7, 2010, 11 pages. (with English Abstract).

*Primary Examiner* — Peter D. Mulcahy
(74) *Attorney, Agent, or Firm* — Oblon, McClelland, Maier & Neustadt, L.L.P.

(57) ABSTRACT

The invention provides a triacrylate compound represented by the following formula (1). In the formula, each R is independently a hydrogen atom, an alkyl group having 1 to 6 carbon atoms or a halogen atom, $R^1$ and $R^2$ are each independently a linear or branched alkyl group having 1 to 6 carbon atoms, and $R^3$ is a linear or branched alkyl group having 1 to 6 carbon atoms or a hydroxymethyl group.

20 Claims, 4 Drawing Sheets

TRIACRYLATE COMPOUNDS AND METHODS FOR PRODUCING THE SAME, AND COMPOSITIONS

TECHNICAL FIELD

The present invention relates to triacrylate compounds and methods for producing such compounds, and to compositions.

BACKGROUND ART

Photocurable resin compositions that are cured by UV lights or electron beams have a short curing time and are advantageous over thermosetting resin compositions in terms of such aspects as resource saving, energy saving and high productivity, thus finding use in a wide range of applications such as inks, paints, coating agents, hard coats, films, adhesives, pressure sensitive adhesives, surface processing agents, lenses, resists, polarizers, sealants, liquid crystals, dental materials and nail cosmetics. Acrylates and methacrylates are widely used in such photocurable resin compositions because of their good curability.

The curable resin compositions sometimes contain triacrylate monomers, trimethacrylate monomers and the like as crosslinking agents or reactive diluents. Some of such triacrylate monomers are trimethylolpropane triacrylate, alkylene oxide-modified trimethylolpropane triacrylate, ditrimethylolpropane triacrylate, alkylene oxide-modified ditrimethylolpropane triacrylate, pentaerythritol triacrylate, alkylene oxide-modified pentaerythritol triacrylate, isocyanurate triacrylate, alkylene oxide-modified isocyanurate triacrylate, glycerol triacrylate and alkylene oxide-modified glycerol triacrylate.

Some example trimethacrylates are those corresponding to the above acrylates except that the acrylate moiety is replaced by methacrylate, namely, trimethylolpropane trimethacrylate, alkylene oxide-modified trimethylolpropane trimethacrylate, ditrimethylolpropane trimethacrylate, alkylene oxide-modified ditrimethylolpropane trimethacrylate, pentaerythritol trimethacrylate, alkylene oxide-modified pentaerythritol trimethacrylate, isocyanurate trimethacrylate, alkylene oxide-modified isocyanurate trimethacrylate, glycerol trimethacrylate and alkylene oxide-modified glycerol trimethacrylate.

These monomers that are generally used, such as trimethylolpropane triacrylate, have high curing shrinkage and thus often come with problems such as cracks during curing, decreased flexibility and curls. To decrease the curing shrinkage or to reduce skin irritancy, the raw material triols are sometimes modified with alkylene oxides and then acrylated. This approach, however, often results in a decrease in curability or crosslinking density by the extension of chain length. Further, extended chains can also cause the viscosity to be increased or the adhesion and weather resistance to be decreased (see, for example, Japanese Patent Application Kokai Publication No. H6-271623; and Kunihiro Ichimura, Dai 5 sho (Chapter 5) Rajikaru jugokei monoma origoma (Radical polymerizable monomers and oligomers), UV kohka no kiso to jissen (Foundation and practice of UV curing), Yoneda Shuppan (Yoneda Publishing), issued Oct. 7, 2010, pp. 55-69). Furthermore, such an alkylene oxide-modified product cannot be obtained as a single compound due to the difficult control of the number of alkylene oxide molecules added, and also tends to be in the form of a peroxide because of having a large number of primary ether bonds and can cause gelation at times.

Thus, there has been a demand for triacrylate compounds as monomers that are balanced in properties such as low curing shrinkage, flexibility, flex resistance, low curling properties, adhesion and curability.

CITATION LIST

Patent Literature

Patent Literature 1: Japanese Patent Application Kokai Publication No. H6-271623

Non-Patent Literature

Non-Patent Literature 1: Kunihiro Ichimura, Dai 5 sho (Chapter 5) Rajikaru jugokei monoma origoma (Radical polymerizable monomers and oligomers), UV kohka no kiso to jissen (Foundation and practice of UV curing), Yoneda Shuppan (Yoneda Publishing), issued Oct. 7, 2010, pp. 55-69

DISCLOSURE OF INVENTION

Technical Problem

In light of the circumstances discussed above, objects of the present invention are to provide triacrylate compounds that exhibit low curing shrinkage when cured and attain an excellent balance of properties such as flex resistance, low curling properties and adhesion, and to provide compositions including the compounds and cured products of the compositions.

Solution to Problem

The present inventors carried out extensive studies directed to achieving the above objects. As a result, the present inventors have developed novel triacrylate compounds and have found that the novel compounds exhibit low curing shrinkage and are excellent in such characteristics as flex resistance and low curling properties, thus completing the present invention. Specifically, some aspects of the present invention reside in the following.

[1] A triacrylate compound represented by the following formula (1):

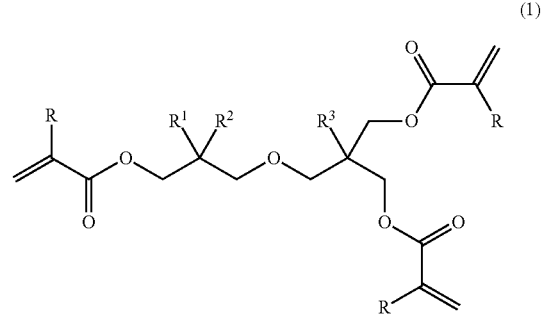

In the formula, each R is independently a hydrogen atom, an alkyl group having 1 to 6 carbon atoms or a halogen atom, $R^1$ and $R^2$ are each independently a linear or branched alkyl group having 1 to 6 carbon atoms, and $R^3$ is a linear or branched alkyl group having 1 to 6 carbon atoms or a hydroxymethyl group.

[2] A composition including the triacrylate compound described in [1], and a radical polymerization initiator.

[3] The composition described in [2], wherein the radical polymerization initiator is a radical photopolymerization initiator.

[4] The composition described in [2] or [3], further including at least one selected from the group consisting of polymerizable monomers other than the triacrylate compound, and polymerizable oligomers.

[5] The composition described in [4], wherein the polymerizable oligomer is at least one kind selected from the group consisting of urethane acrylate oligomers and urethane methacrylate oligomers.

[6] A polymer including a structural unit represented by the following formula (5).

[Chemical Formula 2]

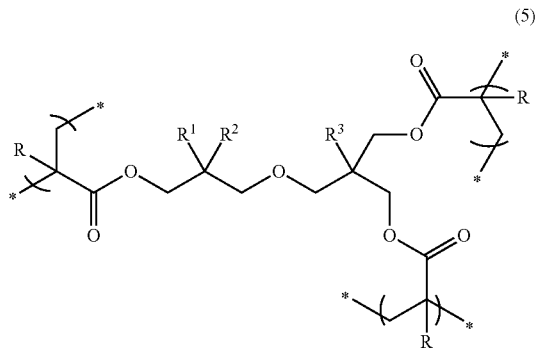

(5)

In the formula, R¹ and R² are each independently a linear or branched alkyl group having 1 to 6 carbon atoms, R³ is a linear or branched alkyl group having 1 to 6 carbon atoms or a hydroxymethyl group, each R is independently a hydrogen atom, an alkyl group having 1 to 6 carbon atoms or a halogen atom, and each * indicates a binding site of the structural unit in the polymer.

[7] A cured product of the composition described in any one of [2] to [5].

[8] An ink including the composition described in any one of [2] to [5].

[9] A coating agent including the composition described in any one of [2] to [5].

[10] A film including a cured product of the composition described in any one of [2] to [5].

[11] An adhesive including the composition described in any one of [2] to [5].

[12] A method for producing a triacrylate compound represented by the formula (1), including subjecting a polyol compound represented by the formula (2) to dehydration condensation reaction with an unsaturated carboxylic acid compound represented by the formula (3a).

[Chemical Formula 3]

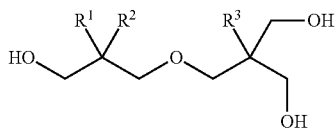
(2)

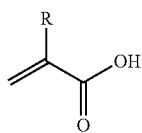
(3a)

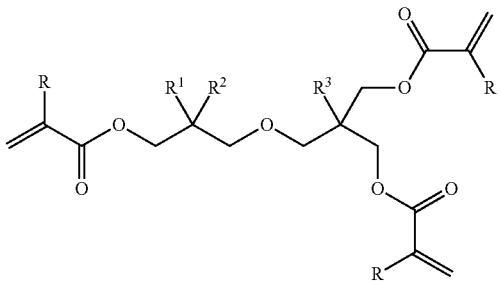
(1)

In the formulae, each R is independently a hydrogen atom, an alkyl group having 1 to 6 carbon atoms or a halogen atom, R¹ and R² are each independently a linear or branched alkyl group having 1 to 6 carbon atoms, and R³ is a linear or branched alkyl group having 1 to 6 carbon atoms or a hydroxymethyl group.

[13] A method for producing a triacrylate compound represented by the formula (1), including subjecting a polyol compound represented by the formula (2) to transesterification reaction with an unsaturated carboxylate ester compound represented by the formula (3b).

[Chemical Formula 4]

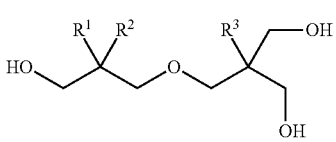
(2)

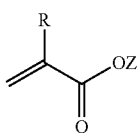
(3b)

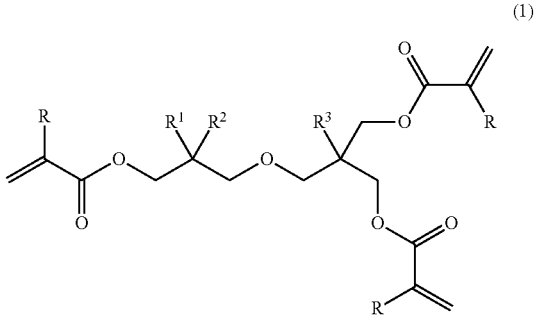
(1)

In the formulae, each R is independently a hydrogen atom, an alkyl group having 1 to 6 carbon atoms or a halogen atom, R¹ and R² are each independently a linear or branched alkyl group having 1 to 6 carbon atoms, R³ is a linear or branched alkyl group having 1 to 6 carbon atoms or a hydroxymethyl group, and Z is an alkyl group having 1 to 6 carbon atoms.

Advantageous Effects of Invention

The triacrylate compounds, the compositions including such compounds and cured products thereof according to the present invention exhibit low curing shrinkage when cured and attain an excellent balance of properties such as flex resistance, low curling properties and adhesion.

BEST MODE FOR CARRYING OUT INVENTION

Figure 1:
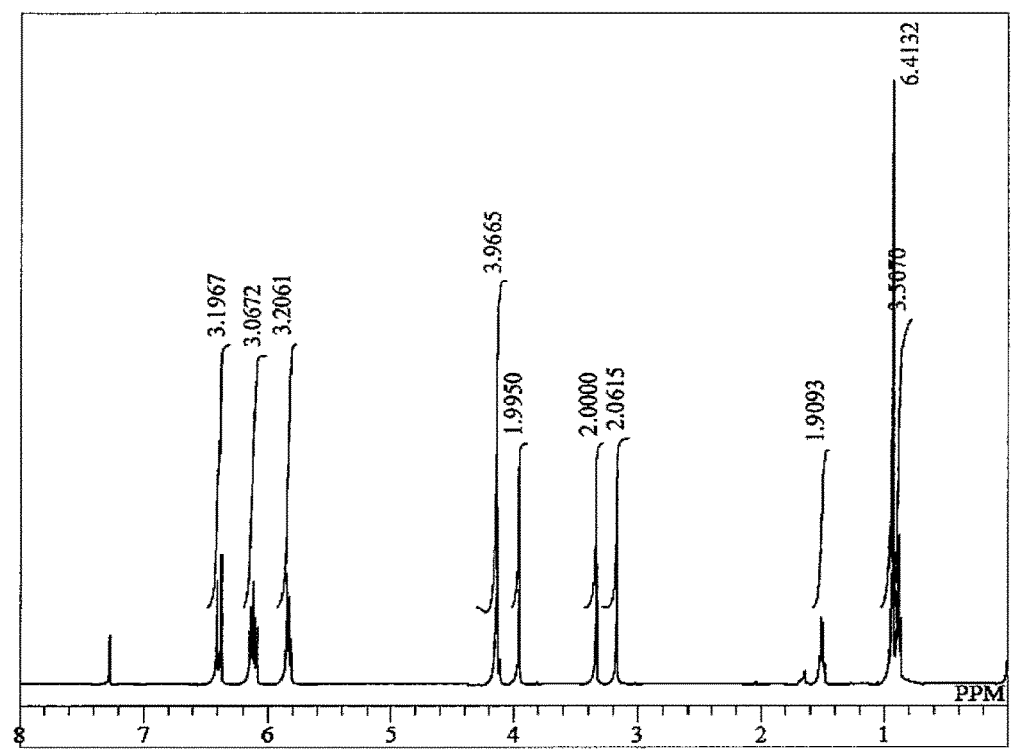
FIG. 1 is a $^1$H-NMR spectrum of a triacrylate compound obtained in Example 1, namely, 2-((3-(acryloyloxy)-2,2-dimethylpropoxy)methyl)-2-ethylpropane-1,3-diyl diacrylate (NTTA).
Figure 2:
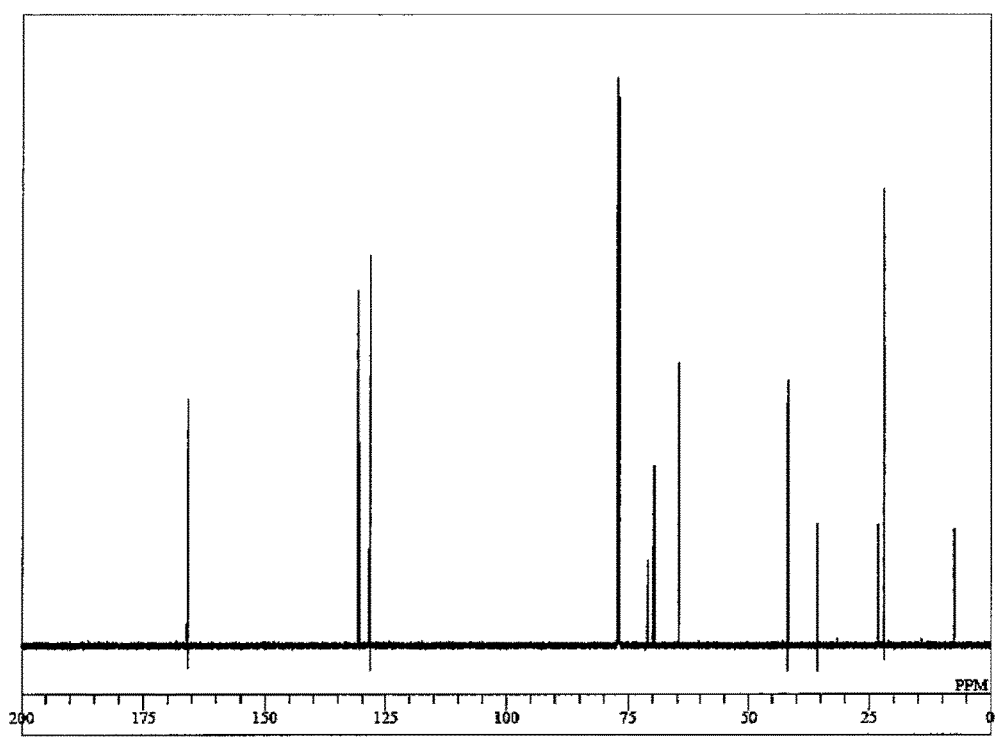
FIG. 2 is a $^{13}$C-NMR spectrum of the triacrylate compound NTTA obtained in Example 1.
Figure 3:
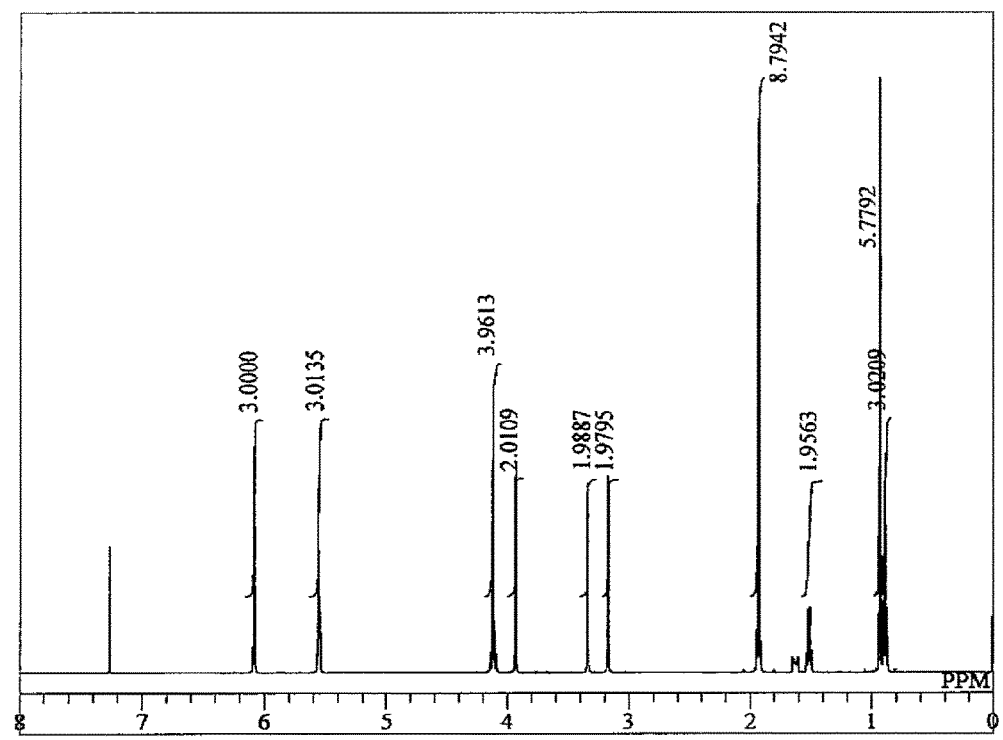
FIG. 3 is a $^1$H-NMR spectrum of a trimethacrylate compound obtained in Example 2, namely, 2-ethyl-2-((3-(methacryloyloxy)-2,2-dimethylpropoxy)methyl)propane-1,3-diyl dimethacrylate (NTTM).
Figure 4:
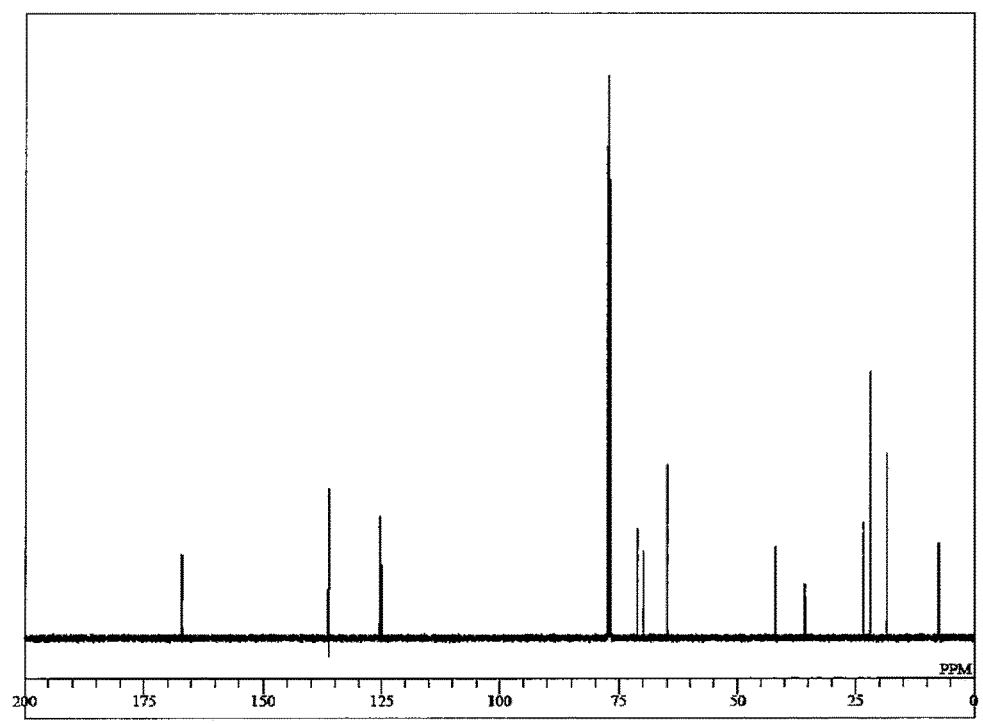
FIG. 4 is a $^{13}$C-NMR spectrum of the trimethacrylate compound NTTM obtained in Example 2.

When a plurality of substances belong to any one component in a specific composition recited in the specification, the content of such a component in the composition means the total content of the plurality of substances present in the composition unless otherwise mentioned. The term "halogen atom" comprehends fluorine atom, chlorine atom, bromine atom and iodine atom.

Hereinbelow, a preferred embodiment of the present invention will be described in detail.

Triacrylate compounds of the present embodiment are represented by the formula (1) described below. The triacrylate compounds represented by the formula (1) show low curing shrinkage when cured, and are excellent in the balance of properties such as flex resistance, low curling properties and adhesion. Further, cured products of such compounds attain excellent properties such as flexibility and weather resistance. The reasons why these advantageous effects are obtained are not clear, but are, for example, probably as described below. In contrast to triacrylate compounds composed of a short carbon chain such as trimethylolpropane triacrylate, the triacrylate compounds represented by the formula (1) have a flexible ether bond structure, and further have a relatively long branched chain structure. These characteristics are probably the reasons why the triacrylate compounds of the formula (1), when polymerized, exhibit low curing shrinkage and attain excellent flex resistance and low curling properties as compared to conventional known triacrylate compounds.

[Chemical Formula 5]

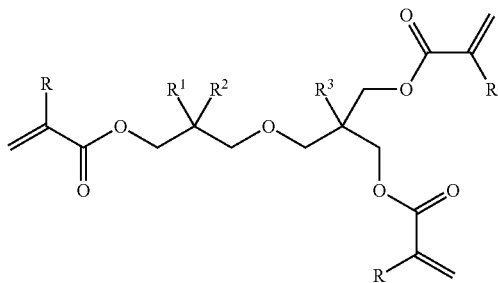

(1)

In the formula, each R is independently a hydrogen atom, an alkyl group having 1 to 6 carbon atoms or a halogen atom, $R^1$ and $R^2$ are each independently a linear or branched alkyl group having 1 to 6 carbon atoms, and $R^3$ is a linear or branched alkyl group having 1 to 6 carbon atoms or a hydroxymethyl group.

In the triacrylate compound represented by the formula (1), each R is preferably a hydrogen atom or an alkyl group having 1 to 3 carbon atoms, and is more preferably a hydrogen atom or a methyl group. $R^1$ and $R^2$ are preferably each independently a linear alkyl group having 1 to 6 carbon atoms, more preferably a linear alkyl group having 1 to 4 carbon atoms, and still more preferably a methyl group. $R^3$ is preferably a linear alkyl group having 1 to 6 carbon atoms, and more preferably a linear alkyl group having 1 or 2 carbon atoms.

In a preferred embodiment of the triacrylate compounds represented by the formula (1), each R is a hydrogen atom or an alkyl group having 1 to 3 carbon atoms, $R^1$ and $R^2$ are each independently a linear alkyl group having 1 to 4 carbon atoms, and $R^3$ is a linear alkyl group having 1 to 6 carbon atoms. In a more preferred embodiment of the triacrylate compounds represented by the formula (1), each R is a hydrogen atom or a methyl group, $R^1$ and $R^2$ are each a methyl group, and $R^3$ is an alkyl group having 1 to 2 carbon atoms.

For example, the triacrylate compound represented by the formula (1) may be produced by a method including reacting a polyol compound represented by the formula (2) with an α,β-unsaturated carbonyl compound represented by the formula (3) so as to form ester bonds.

[Chemical Formula 6]

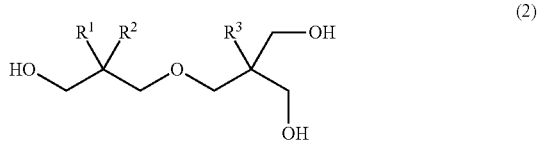

(2)

(3)

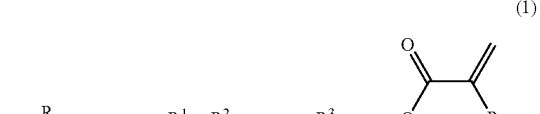

(1)

In the formulae, R and $R^1$ through $R^3$, and preferred embodiments thereof are the same as described above. X is a hydroxyl group, a halogen atom, an alkoxy group having 1 to 6 carbon atoms or an aryloxy group having 6 to 10 carbon atoms. The alkoxy group with 1 to 6 carbon atoms that is represented by X may be linear or branched, and is preferably a linear or branched alkoxy group having 1 to 6 carbon atoms, more preferably a linear or branched alkoxy group having 1 to 4 carbon atoms, and still more preferably an alkoxy group having 1 or 2 carbon atoms.

For example, the polyol compound represented by the formula (2) may be obtained by the hydrogenation reduction of an acetal compound of the formula (4). In the formula, $R^1$ to $R^3$ are the same as described hereinabove. The reaction conditions in the hydrogenation reduction are not particularly limited and may be selected appropriately from usual reaction conditions.

[Chemical Formula 7]

(4)

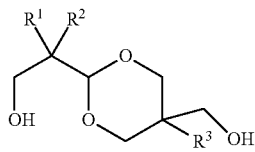

The acetal compound represented by the formula (4) may be obtained by, as illustrated in the reaction formula below, the acetalization of 2,2-disubstituted-3-hydroxypropanal and 2-substituted-2-hydroxymethylpropane-1,3-diol which are readily available. In the reaction formula below, $R^1$ to $R^3$ are as already described hereinabove. The reaction conditions in the acetalization are not particularly limited and may be selected appropriately from usual reaction conditions.

[Chemical Formula 8]

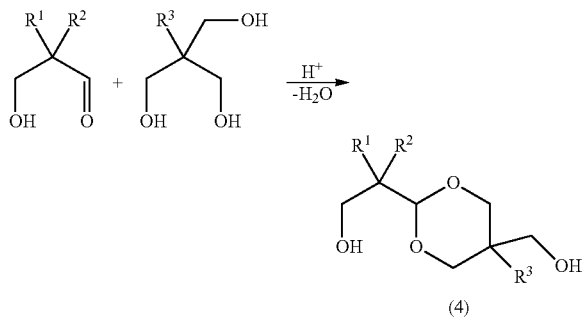

(4)

In the above method for the production of the triacrylate compound represented by the formula (1), examples of the ester bond-forming reactions include dehydration condensation reaction using an α,β-unsaturated carbonyl compound of the formula (3) in which X is a hydroxyl group, namely, an α,β-unsaturated carboxylic acid compound, and transesterification reaction using an α,β-unsaturated carbonyl compound of the formula (3) in which X is an alkoxy group, namely, an α,β-unsaturated carboxylate ester compound.

When dehydration condensation reaction is used in the above method for production, the triacrylate compound represented by the formula (1) may be produced by a method including subjecting a polyol compound represented by the formula (2) to dehydration condensation reaction with an α,β-unsaturated carboxylic acid compound represented by the formula (3a). In the formulae below, R and $R^1$ through $R^3$ are the same as described above.

[Chemical Formula 9]

(2)

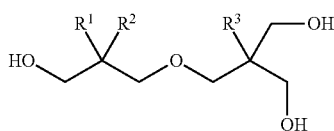

(3a)

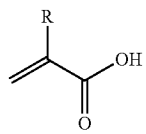

(1)

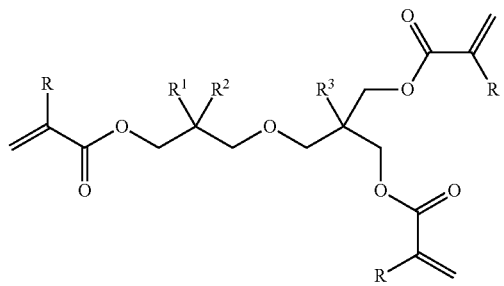

In the dehydration condensation reaction, for example, the polyol compound represented by the formula (2) and the α,β-unsaturated carboxylic acid compound represented by the formula (3a) are preferably used in such amounts that the amount of the α,β-unsaturated carboxylic acid compound is in the range of 3 mol to 10 mol, and more preferably in the range of 3 mol to 5 mol per 1 mol of the polyol compound.

The esterification by the dehydration condensation between the polyol compound represented by the formula (2) and the α,β-unsaturated carboxylic acid compound represented by the formula (3a) may involve an acid catalyst, an organic solvent and a polymerization inhibitor.

Examples of the catalysts which may be used in the esterification by dehydration condensation include known acid catalysts, specifically, inorganic acids such as sulfuric acid, hydrochloric acid and phosphoric acid; organic acids such as methanesulfonic acid, p-toluenesulfonic acid and benzenesulfonic acid; Lewis acids such as boron trifluoride, dimethyltin oxide, dibutyltin oxide, dimethyltin dichloride, dibutyltin dichloride, dimethyldimethoxytin, dibutyldimethoxytin, aluminum isopropoxide, zinc acetylacetonate, tetramethoxytitanium, tetraisopropoxytitanium and tetrabutoxytitanium; and cationic ion-exchange resins. It is preferable to use at least one selected from the group consisting of the above catalysts. The catalysts may be used singly, or two or more may be used at the same time. In an embodiment, a base may be used to generate any of the above Lewis acid catalysts in the reaction system.

When a catalyst is used, the amount of the catalyst is 0.1 mol % to 10 mol %, and preferably 0.5 mol % to 5 mol % relative to 1 mol of the polyol compound.

The organic solvent is not particularly limited as long as it does not undergo side reactions with the raw materials. In particular, a solvent which allows water resulting from the reaction to be distilled off of the system is advantageous in that the reaction is accelerated. That is, a solvent which forms a layer separated from an aqueous layer and can form an azeotrope with water is preferable. Specific examples include aliphatic hydrocarbon solvents such as hexane, heptane, cyclohexane and methylcyclohexane; and aromatic hydrocarbon solvents such as benzene, toluene and xylene. At least one selected from the group consisting of the above solvents may be suitably used. The solvents may be used singly, or two or more may be used in combination.

When an organic solvent is used, for example, the amount of the organic solvent may be a minimum amount required for azeotropic dehydration that is derived from the theoretical amount of water production and the azeotropic ratio of such water to the organic solvent used. The amount of the solvent may be less than the theoretical amount when a Dean-Stark apparatus is used because dehydration may take place while continuously returning the azeotropic solvent back to the reaction vessel. In a simplified case, the amount may be 20 mass % to 200 mass %, and preferably 30 mass % to 100 mass % relative to the total mass of the polyol compound and the unsaturated carboxylic acid compound used.

The polymerization inhibitor is not particularly limited as long as it can scavenge radicals. Specific examples of the polymerization inhibitors include known polymerization inhibitors such as hydroquinone, p-methoxyphenol, t-butylhydroquinone, p-benzoquinone and 2,2,6,6-tetramethylpiperidine-1-oxide. It is preferable to use at least one selected from the group consisting of the above polymerization inhibitors. The polymerization inhibitors may be used singly, or two or more may be used at the same time.

When a polymerization inhibitor is used, the amount of the polymerization inhibitor is, for example, 0.001 mass % to 5 mass %, and preferably 0.01 mass % to 1 mass % relative to the α,β-unsaturated carboxylic acid compound.

When transesterification reaction is used, the triacrylate compound represented by the formula (1) may be produced by a method including subjecting a polyol compound represented by the formula (2) to transesterification reaction with an α,β-unsaturated carboxylate ester compound represented by the formula (3b). In the formulae below, R and $R^1$ through $R^3$ are the same as described above. Z represents an alkyl group having 1 to 6 carbon atoms, and may be linear or branched.

[Chemical Formula 10]

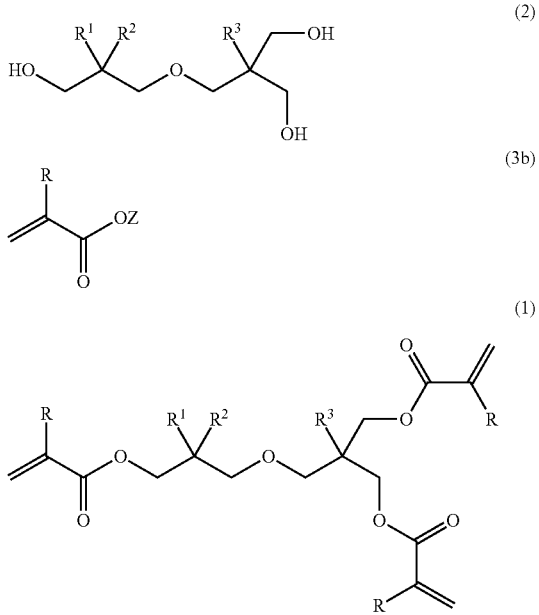

The alkyl group represented by Z is preferably a lower alkyl group, more preferably a linear or branched alkyl group having 1 to 4 carbon atoms, and more preferably an alkyl group having 1 or 2 carbon atoms. Specific examples of the alkyl groups represented by Z include methyl group, ethyl group, propyl group, isopropyl group, butyl group, isobutyl group and tert-butyl group. In particular, Z is preferably a methyl group or an ethyl group, and more preferably a methyl group in view of the fact that the alcohol resulting from the transesterification reaction may be removed easily.

In the transesterification reaction, for example, the polyol compound represented by the formula (2) and the α,β-unsaturated carboxylate ester compound represented by the formula (3b) are preferably used in such amounts that the amount of the α,β-unsaturated carboxylate ester compound is in the range of 3 mol to 20 mol, and more preferably in the range of 3 mol to 10 mol per 1 mol of the polyol compound.

The manner in which the transesterification reaction is performed is not particularly limited. Because the reaction is allowed to take place rapidly by removing the lower alcohol resulting from the reaction out of the reaction system, the reactor is preferably equipped with a distillation column so that the reaction is performed while distilling off the lower alcohol. The transesterification reaction may involve a catalyst, a polymerization inhibitor or the like. The details of the polymerization inhibitor are similar to those described with respect to the esterification by the dehydration condensation of the α,β-unsaturated carboxylic acid compound, except that the amount of the polymerization inhibitor is expressed relative to the α,β-unsaturated carboxylate ester compound instead of the α-β-unsaturated carboxylic acid compound.

The catalyst for the transesterification reaction may be a Lewis acid catalyst, a base catalyst or the like. The Lewis acid catalyst may be a known Lewis acid catalyst, with examples including dimethyltin oxide, dibutyltin oxide, dimethyltin dichloride, dibutyltin dichloride, dimethyldimethoxytin, dibutyldimethoxytin, aluminum isopropoxide, zinc acetylacetonate, tetramethoxytitanium, tetraisopropoxytitanium and tetrabutoxytitanium. It is preferable to use at least one selected from the group consisting of the above catalysts. In an embodiment, a base may be used to generate any of the above Lewis acid catalysts in the reaction system.

Examples of the known base catalysts for use in the transesterification reaction include lithium methoxide, sodium methoxide, potassium methoxide, lithium ethoxide, sodium ethoxide and potassium ethoxide. It is preferable to use at least one selected from the group consisting of the above catalysts. The catalysts may be used singly, or two or more may be used at the same time appropriately while ensuring that any problems will not be caused.

When the transesterification reaction involves a catalyst, the amount of the catalyst is 0.1 mol % to 10 mol %, and preferably 0.5 mol % to 5 mol % relative to 1 mol of the polyol compound.

The transesterification reaction may involve an organic solvent as required. The details of the organic solvent are similar to those described with respect to the esterification by the dehydration condensation of the α,β-unsaturated carboxylic acid compound, except that the amount of the organic solvent is expressed relative to the α,β-unsaturated carboxylate ester compound instead of the α-β-unsaturated carboxylic acid compound.

The triacrylate compounds represented by the formula (1) may be used as, for example, crosslinking agents, reactive diluents, viscosity modifiers and the like in applications such as inks, paints, coating agents, hard coats, films, adhesives, pressure sensitive adhesives, surface processing agents, lenses, resists, polarizers, sealants, liquid crystal display materials, color filter materials, dental materials and nail cosmetics.

The scope of the present invention includes, in addition to the triacrylate compounds represented by the general formula (1), diacrylate compounds represented by the formula (6) below. The diacrylate compounds represented by the formula (6), when polymerized, exhibit low curing shrinkage and attain excellent flex resistance and low curling properties.

[Chemical Formula 11]

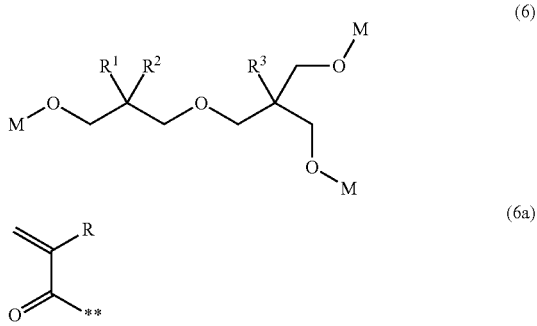

R and $R^1$ through $R^3$ are defined the same as R and $R^1$ through $R^3$ in the formula (1). Two of the substituents M are groups represented by the formula (6a), and the other is a hydrogen atom. The asterisks ** represent that M is bonded at the indicated position. A diacrylate compound represented by the formula (6) is by produced at times during the production of a compound represented by the formula (1), or may be produced using the same raw materials while changing the ratio of the raw materials appropriately.

The triacrylate compound represented by the formula (1) may be polymerized to give a cured product. In accordance with the application, the triacrylate compound may be polymerized singly or may be copolymerized with other polymerizable monomer or polymerizable oligomer. The copolymerization may involve two or more kinds of other polymerizable monomers and polymerizable oligomers at the same time. That is, the triacrylate compound represented by the formula (1) may constitute a composition (preferably, a polymerizable composition) which includes at least one triacrylate compound and at least one radical polymerization initiator, or may constitute a composition (preferably, a polymerizable composition) which further includes at least one selected from the group consisting of polymerizable monomers other than the triacrylate compounds, and polymerizable oligomers.

The additional polymerizable monomers and polymerizable oligomers are not particularly limited, and may be selected appropriately from usual polymerizable compounds in accordance with factors such as purposes. The additional polymerizable monomers may be any polymerizable monomers other than the triacrylate compounds represented by the formula (1). Examples thereof include acrylic monomers having an acrylic group, methacrylic monomers having a methacrylic group, and styrene derivatives.

Specific examples of the acrylic monomers include methyl acrylate, ethyl acrylate, propyl acrylate, dicyclopentenyl acrylate, dicyclopentanyl acrylate, isobornyl acrylate, tetrahydrofurfuryl acrylate, phenoxyethyl acrylate, lauryl acrylate, 2-hydroxyethyl acrylate, polypropylene glycol diacrylate, neopentyl glycol diacrylate, dineopentyl glycol diacrylate, trimethylolpropane triacrylate, pentaerythritol tetraacrylate, ditrimethylolpropane tetraacrylate and dipentaerythritol hexaacrylate. It is preferable to use at least one selected from the group consisting of the above monomers. Further, specific examples of the methacrylic monomers having a methacrylic group include methyl methacrylate, ethyl methacrylate, propyl methacrylate, dicyclopentenyl methacrylate, dicyclopentanyl methacrylate, isobornyl methacrylate, tetrahydrofurfuryl methacrylate, phenoxyethyl methacrylate, lauryl methacrylate, 2-hydroxyethyl methacrylate, polypropylene glycol dimethacrylate, neopentyl glycol dimethacrylate, dineopentyl glycol dimethacrylate, trimethylolpropane trimethacrylate, pentaerythritol tetramethacrylate, ditrimethylolpropane tetramethacrylate and dipentaerythritol hexamethacrylate. It is preferable to use at least one selected from the group consisting of the above monomers. The additional polymerizable monomers may be used singly, or two or more may be used in combination.

Examples of the polymerizable oligomers include polymerizable compounds obtained by the acrylation or methacrylation of oligomers including two or more structural units. Specific examples include polyester acrylate, epoxy acrylate, polyether acrylate, urethane acrylate, polycarbonate diol acrylate, polycarbonate diol urethane acrylate, polyester methacrylate, epoxy methacrylate, polyether methacrylate, urethane methacrylate, polycarbonate diol methacrylate and polycarbonate diol urethane methacrylate. It is preferable to use at least one selected from the group consisting of the above oligomers. It is more preferable that the composition include at least one selected from urethane acrylate oligomers and urethane methacrylate oligomers. It is still more preferable that the composition include at least one selected from aliphatic urethane acrylate oligomers and aliphatic urethane methacrylate oligomers. The polymerizable oligomers may be used singly, or two or more may be used in combination. The polymerizable oligomers may be used in combination with at least one of the additional polymerizable monomers. The molecular weight of the polymerizable oligomers is not particularly limited. The molecular weight is, for example, 500 to 40000, preferably 800 to 5000, and more preferably 2000 to 5000 when expressed as weight average molecular weight. The molecular weight of the polymerizable oligomers is the weight average molecular weight and is measured by gel permeation chromatography (GPC).

For example, the polymerizable oligomer has an oligomer chain moiety and, at an end thereof, a polymerizable group derived from acrylic acid or methacrylic acid or from an ester thereof. For example, the oligomer chain moiety is a structure formed by the removal of a hydrogen atom from a terminal functional group in an oligomer such as a terminal hydroxyl or amino group. Some example oligomers that can form the oligomer chain moieties are at least one selected from the group consisting of polyalkylene oxides such as polyethylene oxide and polypropylene oxide, aliphatic or aromatic polyester diols, aliphatic or aromatic polyamides, and aliphatic or aromatic polycarbonate diols, or any combinations or derivatives of these oligomers; aliphatic or aromatic epoxy resins; and homopolymers and copolymers of at least one monomer selected from the group consisting of alkyl acrylates, alkyl methacrylates, styrene and derivatives thereof, acrylonitrile, vinyl acetate and butadiene. Of these, alkylene oxides and aliphatic oligomers having a terminal hydroxyl group such as aliphatic polyester diols and aliphatic polycarbonate diols are preferable. The oligomer chains may be linear or branched.

The polymerizable oligomer has a polymerizable group at an end of the oligomer chain. The polymerizable oligomer may be a compound which includes an ester bond, an amide bond or the like formed between acrylic acid or methacrylic acid and the terminal functional group of the oligomer chain, or may be a urethane acrylate oligomer or a urethane methacrylate oligomer which includes a urethane bond formed between a hydroxyalkyl ester of acrylic acid or methacrylic acid and a polyfunctional isocyanate compound. The number of polymerizable groups in the polymerizable oligomer is not particularly limited, and is, for example, 2 to 3.

The hydroxyalkyl ester of acrylic acid or methacrylic acid in the urethane acrylate oligomer is preferably at least one selected from the group consisting of 2-hydroxyethyl acrylate, trimethylolpropane diacrylate, pentaerythritol triacrylate and dipentaerythritol pentaacrylate, and 2-hydroxyethyl methacrylate, trimethylolpropane dimethacrylate, pentaerythritol trimethacrylate and dipentaerythritol pentamethacrylate. The polyfunctional isocyanate compound is preferably at least one selected from the group consisting of isophorone diisocyanate (IPDI), 4,4'-dicyclohexylmethane diisocyanate (hydrogenated MDI), hexamethylene diisocyanate (HDI), trimethylhexamethylene diisocyanate (TMDI), 4,4'-diphenylenemethane diisocyanate (MDI), methylcyclohexylene diisocyanate (hydrogenated TDI) and 2,4-tolylene diisocyanate (TDI). The polyisocyanates may be used singly, or two or more may be used in combination.

In a composition, the ratio of the content of the triacrylate compound represented by the formula (1) and that of at least one selected from the group consisting of additional polymerizable monomers and polymerizable oligomers is not particularly limited and may be selected appropriately in accordance with factors such as purposes. With respect to the polymerizable compounds present in the composition, the content of the triacrylate compound represented by the formula (1) on the mass basis is, for example, 5 mass % to 70 mass %, and preferably 5 mass % to 50 mass %.

A composition including the triacrylate compound represented by the formula (1) and a radical polymerization initiator can form a cured product upon radical photopolymerization or thermal radical polymerization. It is preferable that the composition include at least a radical photopolymerization initiator.

The radical polymerization initiator is not particularly limited and may be selected appropriately from general radical polymerization initiators in accordance with factors such as purposes. Examples of the radical polymerization initiators include radical photopolymerization initiators such as acetophenone, p-anisyl, benzoin, benzoin methyl ether, benzoin isobutyl ether, dibenzoyl and 1-hydroxycyclohexyl phenyl ketone; and thermal radical polymerization initiators such as 2,2'-azobis(isobutyronitrile), 2,2'-azobis(2,4-dimethylvaleronitrile) and benzoyl peroxide. It is preferable to use at least one selected from the group consisting of the above initiators. The radical polymerization initiators may be used singly, or two or more may be used in combination.

When the composition contains a radical polymerization initiator, the content thereof is, for example, 1 mass % to 20 mass %, and preferably 1 mass % to 5 mass % relative to the total mass of the polymerizable monomer(s) and polymerizable oligomer(s).

The composition may further contain various additives as required. The composition may easily attain desired properties by containing various additives. Example of the additives include pigments, dyes, antifoaming agents, anti-sagging agents, adhesion promoters, plasticizers, dispersants, surface leveling agents, viscosity modifiers, antistatic agents, mold release agents, light diffusing agents and antioxidants. It is possible to add inorganic fillers such as glass fibers, carbon fibers and clay compounds. These additives may be used singly, or two or more may be used in combination.

The composition can be used without a solvent, or may further contain an organic solvent depending on factors such as the type of a substrate and the type of a coating method. The organic solvent is not particularly limited and may be selected appropriately from usual organic solvents in accordance with factors such as purposes. Specific examples of the organic solvents include aliphatic hydrocarbon solvents such as hexane and heptane: aromatic hydrocarbon solvents such as toluene and xylene; alcohol solvents such as methanol and ethanol; ether solvents such as diethyl ether, tetrahydrofuran and 1,4-dioxane; ester solvents such as ethyl acetate; and ketone solvents such as acetone, methyl ethyl ketone and cyclohexanone. The organic solvents may be used singly, or two or more may be used in combination.

When the composition includes an organic solvent, the content thereof is not particularly limited and may be selected appropriately in accordance with factors such as purposes. For example, the content of the organic solvent may be such that the amount of nonvolatile components in the composition (the solid content) will be 70 mass % to 95 mass %.

The scope of the present invention includes cured products of the composition described above. Such cured products attain a good balance of properties such as low curing shrinkage, high flex resistance, adhesion and low curling properties.

The method for curing the composition is not particularly limited and is selected appropriately from usual methods in accordance with factors such as the type of the radical polymerization initiator present in the composition. The composition may be cured by heat treatment or irradiation treatment. The irradiation treatment may be followed by heat treatment. The heat treatment temperature may be, for example, 60° C. to 200° C., and the heat treatment time may be, for example, 10 minutes to 3 hours. The irradiation treatment may be performed by applying light having a wavelength of, for example, 210 nm to 450 nm. The dose may be, for example, not less than 80 mJ/cm$^2$.

The scope of the present invention includes polymers including a structural unit represented by the formula (5) below (hereinafter, also written simply as "polymers"). By its containing a structural unit represented by the formula (5), the polymer attains a good balance of properties such as low curing shrinkage, high flex resistance, adhesion and low curling properties.

[Chemical Formula 12]

(5)

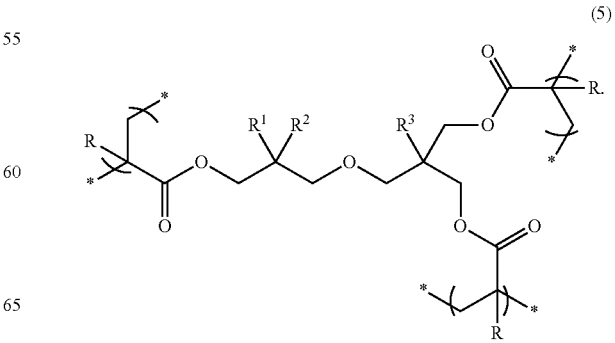

$R^1$ and $R^2$ are each independently a linear or branched alkyl group having 1 to 6 carbon atoms, $R^3$ is a linear or branched alkyl group having 1 to 6 carbon atoms or a hydroxymethyl group, each R is independently a hydrogen atom, an alkyl group having 1 to 6 carbon atoms or a halogen atom, and each * indicates a binding site of the structural unit in the polymer.

The polymer is not limited as long as it includes structural units represented by the formula (5), and may contain at least one type of structural units derived from other polymerizable monomers and polymerizable oligomers. The details of such additional polymerizable monomers and polymerizable oligomers are the same as described hereinabove. It is preferable that the polymer include at least one type of structural units derived from polymerizable oligomers, more preferably include at least one type of structural units selected from those derived from urethane acrylate oligomers and those derived from urethane methacrylate oligomers, and still more preferably include at least one type of structural units selected from those derived from aliphatic urethane acrylate oligomers and those derived from aliphatic urethane methacrylate oligomers. Here, the term "structural unit" means a partial structure formed by the polymerization of monomer molecules that constitute the polymer.

When the polymer contains structural units derived from additional polymerizable monomers and polymerizable oligomers, the content of the structural units represented by the formula (5) on the mass basis is, for example, 5 mass % to 70 mass %, and preferably 5 mass % to 50 mass %.

The molecular weight of the polymers is not particularly limited and may be selected appropriately in accordance with factors such as purposes. The weight average molecular weight of the polymers is, for example, 1000 to 40000.

The polymer may include, in addition to the structural unit represented by the formula (5), a structural unit represented by the formula (7) below.

[Chemical Formula 13]

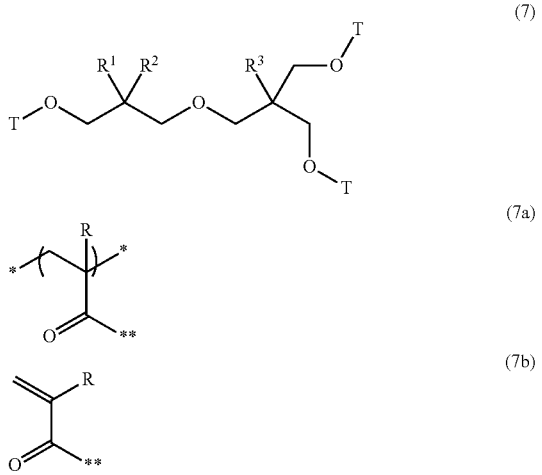

$R^1$, $R^2$, $R^3$ and R are the same as defined above. Each T is independently a group represented by the formula (7a) or the formula (7b), and one or two of Ts are represented by the formula (7a). The asterisk ** represents a binding site in T, and the asterisk * represents a binding site of the structural unit in the polymer.

The structural unit represented by the formula (7) may be such that two Ts are represented by the formula (7a) or one T is represented by the formula (7a). When two Ts are represented by the formula (7a), the polymer will have a crosslink structure represented by the formula (7).

For example, the polymer may be produced by curing a composition including a triacrylate compound represented by the formula (1). That is, the polymer is a cured product obtained by curing the aforementioned composition.

The scope of the present invention includes inks including the above-described composition. Such an ink includes a triacrylate compound represented by the formula (1) and a radical polymerization initiator, and further includes, for example, a colorant. The colorant may be any of pigments and dyes, and is selected appropriately from usual pigments and dyes in accordance with factors such as purposes. Specific examples of the pigments include organic pigments such as azo pigments, polycyclic pigments, nitro pigments, nitroso pigments and aniline blacks; and inorganic pigments such as carbon blacks, metal oxides, metal sulfides, metal chlorides, aluminum powder, silica and calcium carbonate.

The content of the colorant present in the ink is not particularly limited and is selected appropriately in accordance with factors such as purposes. For example, the content of the colorant is 1 mass % to 30 mass % of the total mass of the ink.

The scope of the present invention includes coating agents including the above-described composition. Such a coating agent may be applied onto a desired member to form a composition layer, which is then cured to form on the member a coat layer that is a cured product of the composition. The member to which the coating agent is applied is not particularly limited, and a desired member may be provided appropriately in accordance with factors such as purposes. The method for applying the coating agent is selected appropriately from usual methods in accordance with factors such as the type of a member and the formulation of the coating agent. Some example application methods are coating, spraying and dipping.

The scope of the present invention includes films including a cured product of the above-described composition. The film may be produced by applying a composition which includes a triacrylate compound represented by the formula (1) and a radical polymerization initiator onto a substrate, curing the coating, and separating the resultant film from the substrate. The thickness of the films is not particularly limited and is selected appropriately in accordance with factors such as purposes. For example, the thickness of the film is 5 μm to 200 μm.

The scope of the present invention includes adhesives including the above-described composition. For example, the adhesive may be applied between a first member and a second member to form an adhesive layer, and this layer may be cured to bond the first member and the second member to each other. The members to which the adhesive is applied are not particularly limited, and desired members may be provided appropriately in accordance with factors such as purposes. The first member and the second member may be the same as or different from each other. The adhesive has low curing shrinkage and exhibits excellent adhesion.

EXAMPLES

Hereinbelow, the present invention will be described in greater detail based on Examples. However, the scope of the invention is not limited to such Examples presented below.

The following is information such as the abbreviations and manufacturers of the raw materials used in Examples and Comparative Examples, and pretreatments performed on the raw materials.

TMPTA: trimethylolpropane triacrylate (manufactured by Tokyo Chemical Industry Co., Ltd.)

TMPTM: trimethylolpropane trimethacrylate (manufactured by Tokyo Chemical Industry Co., Ltd.)

Because of a purity of 79%, TMPTA above was used after column purification.

Urethane oligomer: trade name "SHIKOH UV-7510B" manufactured by The Nippon Synthetic Chemical Industry Co., Ltd.

Polymerization initiator: 1-hydroxycyclohexyl phenyl ketone (manufactured by Wako Pure Chemical Industries, Ltd.)

The reaction was analyzed by gas chromatography. The gas chromatograph used was 7890A manufactured by Agilent Technologies Japan, Ltd. The column used was DB-1701 manufactured by J & W Co., Ltd. The column temperature was held at 40° C. for 5 minutes, increased to 250° C. at 10° C./min, and held constant for 35 minutes. The injection temperature was 210° C. TCD was used as the detector at 250° C. Helium was used as the carrier gas.

The product was identified by $^1$H-NMR and $^{13}$C-NMR spectroscopy. The measurements were performed in CDCl$_3$ solvent at 500 MHz and 125 MHz, respectively.

In the measurement, JNM-ECA500 manufactured by JEOL Ltd. was used.

Synthetic Example 1

Synthesis of 2-(5-ethyl-5-hydroxymethyl-[1,3]dioxan-2-yl)-2-methylpropan-1-ol

A 2-liter round bottomed flask was loaded with 45.1 g of 2,2-dimethyl-3-hydroxypropionaldehyde (hydroxypivalaldehyde, manufactured by MITSUBISHI GAS CHEMICAL COMPANY, INC., purity 99.8%), 59.6 g of 2-ethyl-2-hydroxymethylpropane-1,3-diol (trimethylolpropane, reagent manufactured by Tokyo Chemical Industry Co., Ltd.), 706 g of benzene, and 5.0 g of granular Nafion (trade name "NR-50", reagent manufactured by Sigma-Aldrich Co. LLC.). The reaction was performed at ordinary pressure while discharging byproduct water as an azeotrope with benzene out of the reaction system with use of a Dean-Stark trap until the distillation of water ceased. The product was filtered, concentrated and cooled to recrystallize. In this manner, a crystal of 2-(5-ethyl-5-hydroxymethyl-[1,3]dioxan-2-yl)-2-methylpropan-1-01 was obtained.

[Chemical Formula 14]

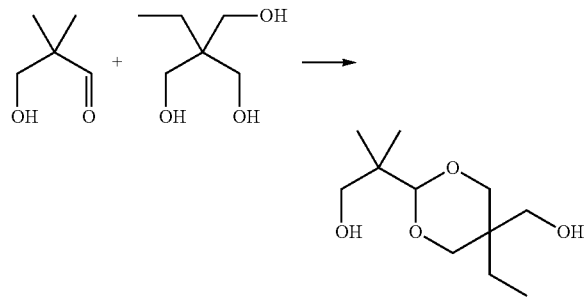

A catalyst for use in the hydrogenation of acetal was synthesized as follows.

Preparation of Carrier

Zirconium oxide used as a carrier for metal components was prepared by the following method.

While performing stirring, 15.5 g of 28 mass % ammonia water was added dropwise to 505 g of an aqueous zirconium oxynitrate solution having a concentration in terms of zirconium oxide (ZrO$_2$) of 25 mass %, resulting in a white precipitate. The precipitate was removed by filtration, washed with ion-exchanged water, and dried at 110° C. for 10 hours to give hydrous zirconium oxide. The oxide was placed into a porcelain crucible, calcined in the air with use of an electric furnace at 400° C. for 3 hours, and crushed in an agate mortar to give powdery zirconium oxide (hereinafter, also written as the "carrier A"). The BET specific surface area of the carrier A (measured by the nitrogen adsorption method) was 102.7 m$^2$/g.

Preparation of Catalyst

A catalyst having palladium as a specific metal component was prepared by the following method.

An aqueous solution of 0.66 mass % palladium chloride and 0.44 mass % sodium chloride was added to 50 g of the carrier A, and the metal components were adsorbed on the carrier. An aqueous formaldehyde-sodium hydroxide solution was poured to the carrier to reduce instantaneously the metal components adsorbed. Thereafter, the catalyst was washed with ion-exchanged water and was dried to give a 1.0 mass % palladium-supporting zirconium oxide catalyst (hereinafter, written as the "catalyst A").

Synthetic Example 2

Synthesis of 2-ethyl-2-(3-hydroxy-2,2-dimethyl-propoxymethyl)-propane-1,3-diol

A 500 mL SUS reactor was loaded with 7.5 g of the catalyst A, 75 g of 2-(5-ethyl-5-hydroxymethyl-[1,3]dioxan-2-yl)-2-methylpropan-1-ol, and 225 g of dioxane. The reactor was then purged with nitrogen gas. Thereafter, 8.5 MPa hydrogen gas was fed into the reactor. The temperature was increased to a prescribed reaction temperature of 230° C., and the reaction was performed for 8 hours. After being cooled, the product in the reactor was recovered and recrystallized to give the target compound.

[Chemical Formula 15]

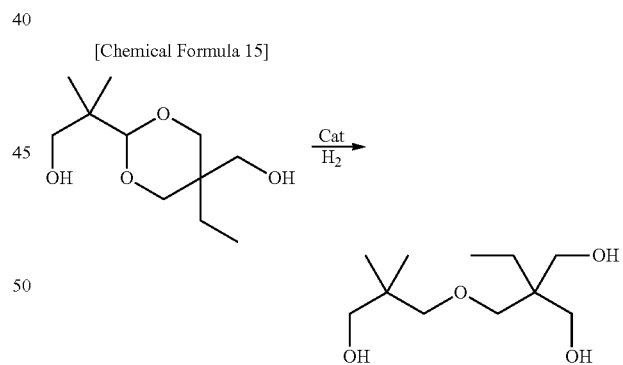

Example 1

Synthesis of 2-((3-(acryloyloxy)-2,2-dimethyl-propoxy)methyl)-2-ethylpropane-1,3-diyl diacrylate (NTTA)

In a glass reactor equipped with a stirring bar, a thermometer and a Vigreux column were mixed 2-ethyl-2-(3-hydroxy-2,2-dimethyl-propoxymethyl)-propane-1,3-diol (30.0 g, 136 mmol), methyl acrylate (59.3 g, 680 mmol), dimethyltin dichloride (900 mg, 4.1 mmol), sodium methoxide (216 mg, 4.1 mmol), p-methoxyphenol (297 mg, 2.4 mmol)

and hydroquinone (120 mg, 1.1 mmol). The mixture was heated at an internal temperature of not less than 82° C. and not more than 94° C. While distilling off methanol from the system as an azeotrope with methyl acrylate, stirring was performed for 30 hours while performing heating. During the reaction, a 1 mass % p-methoxyphenol solution of methyl acrylate was added dropwise from the column top, thereby preventing polymerization in the Vigreux column and making up for the loss of methyl acrylate by azeotropic distillation of methanol. The catalyst and the polymerization inhibitor were removed by base washing, and the unreacted methyl acrylate was distilled off under reduced pressure. Consequently, the target triacrylate monomer was obtained (49.4 g, purity 93.5%, 121 mmol, 89% yield).

(Compound NTTA)

The product obtained in Example 1 was identified by $^1$H-NMR and $^{13}$C-NMR spectroscopy to be a novel compound represented by the following chemical structural formula. In the specification, this compound is sometimes written as NTTA.

[Chemical Formula 16]

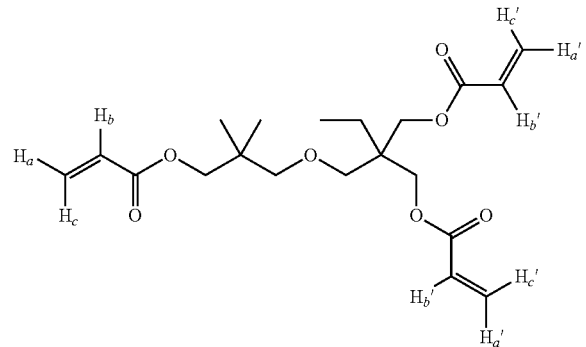

NTTA: oily, colorless.

$^1$H-NMR δ 0.88 (t, —CH$_2$C$\underline{H}_3$, 3H), 0.93 (s, —C(C$\underline{H}_3$)$_2$, 6H), 1.50 (q, —C$\underline{H}_2$CH$_3$, 2H), 3.16 (s, —C$\underline{H}_2$O—, 2H), 3.30 (s, —C$\underline{H}_2$O—, 2H), 3.95 (s, —COOC$\underline{H}_2$—, 2H), 4.13-4.14 (m, —COOC$\underline{H}_2$×2, 4H), 5.81-5.84 (m, $\underline{H}_a$&$\underline{H}_a$', 3H), 6.08-6.15 (m, $\underline{H}_b$&$\underline{H}_b$', 3H), 6.37-6.40 (m, $\underline{H}_c$&$\underline{H}_c$'3H).

$^{13}$C-NMR δ 7.46, 21.87, 23.17, 35.69, 41.77, 64.64, 69.67, 70.94, 77.21, 128.22, 128.23, 128.50, 130.42, 130.83, 165.89, 166.05.

Example 2

Synthesis of 2-ethyl-2-((3-(methacryloyloxy)-2,2-dimethylpropoxy)methyl)propane-1,3-diyl dimethacrylate (NTTM)

In a glass reactor equipped with a stirring bar, a thermometer and a Vigreux column were mixed 2-ethyl-2-(3-hydroxy-2,2-dimethyl-propoxymethyl)-propane-1,3-diol (30.0 g, 136 mmol), methyl methacrylate (109 g, 1.09 mol), dimethyltin dichloride (902 mg, 4.1 mmol), sodium methoxide (220 mg, 4.1 mmol) and p-methoxyphenol (125 mg, 1.0 mmol). The mixture was heated at an internal temperature of not less than 93° C. and not more than 115° C. While distilling off methanol from the system as an azeotrope with methyl methacrylate, stirring was performed for 42 hours while performing heating. The catalyst and the polymerization inhibitor were removed by base washing, and the unreacted methyl methacrylate was distilled off under reduced pressure. Consequently, the target trimethacrylate monomer was obtained (58.7 g, purity 92.2%, 127 mmol, 94% yield).

(Compound NTTM)

The product obtained in Example 2 was identified by $^1$H-NMR and $^{13}$C-NMR spectroscopy to be a novel compound represented by the following chemical structural formula. In the specification, the compound is sometimes written as NTTM.

[Chemical Formula 17]

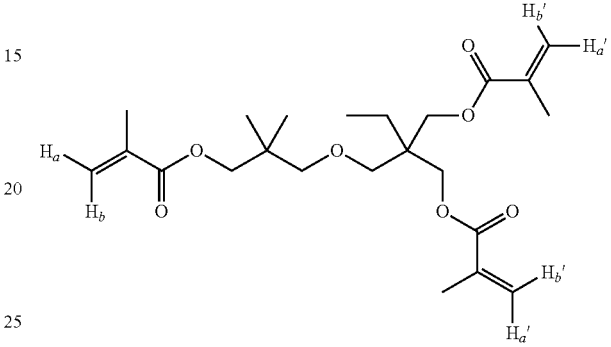

NTTM: oily, colorless.

$^1$H-NMR δ 0.89 (t, —CH$_2$C$\underline{H}_3$, 3H), 0.93 (s, —C(C$\underline{H}_3$)$_2$, 6H), 1.51 (q, —C$\underline{H}_2$CH$_3$, 2H), 1.93 (s, CH$_2$=C(C$\underline{H}_3$)CO—×3, 9H), 3.17 (s, —C$\underline{H}_2$O—, 2H), 3.33 (s, —C$\underline{H}_2$O—, 2H), 3.93 (s, —COOC$\underline{H}_2$—, 2H), 4.11-4.12 (m, —COOC$\underline{H}_2$×2, 4H), 5.54-5.55 (m, $\underline{H}_a$&$\underline{H}_a$'×2, 3H), 6.08 (s, $\underline{H}_b$&$\underline{H}_b$'×2, 3H).

$^{13}$C-NMR δ 7.53, 18.29, 21.92, 23.36, 35.78, 41.96, 64.79, 69.83, 71.11, 77.32, 125.14, 125.57, 136.17, 136.44, 167.05, 167.19.

<Evaluation>

In the following, the triacrylate monomer and the trimethacrylate monomer synthesized in Examples 1 and 2 were UV cured severally, and the properties of the cured products were evaluated as described below. Separately, cured products of generally-used trimethylolpropane triacrylate (TMPTA) and trimethylolpropane trimethacrylate (TMPTM) were tested similarly to evaluate their properties.

Curing Shrinkage:

The specific gravity of the monomer before curing was measured with a pycnometer. With use of an electronic hydrometer (μW-300SG manufactured by Alfa Mirage Co., Ltd.), the specific gravity of a 0.5 mm thick cured plate was measured. The curing shrinkage (%) was calculated using the following equation.

Curing shrinkage (%)=[{(Specific gravity of cured product)−(Specific gravity before curing)}/(Specific gravity of cured product)]×100

Pencil Hardness:

A cured film with a thickness of 50 μm formed on a 0.5 mm thick polycarbonate substrate was tested in accordance with JIS K 5600-5-4 using a pencil hardness tester manufactured by COTEC to determine the pencil hardness.

Adhesion:

A cured film with a thickness of 50 μm formed on a 125 μm thick surface-treated PET film (trade name "Cosmo Shine A2330" manufactured by TOYOBO CO., LTD.) was tested by a cross-cut tape method in accordance with JIS K 5400-8-5-2 using a cross-cut guide manufactured by COTEC. The degree of separation per 100 squares was evaluated using the following formula.

(Number of squares that remained without separation)/100

Curling Properties:

A cured film with a thickness of 23 μm or 50 μm was formed on a 100 μm thick polycarbonate film (trade name "Iupilon film FE-2000" manufactured by MITSUBISHI GAS CHEMICAL COMPANY, INC.). The cured film, together with the polycarbonate film, was cut into a 100 mm×100 mm test piece. The test piece was placed on a horizontal plate, and the lifting from the plate surface was measured with respect to the four corners of the test piece. The average of the liftings of the four corners was indicated as the measured value of curling properties.

Example 3

To NTTA (12.0 g) produced in Example 1, polymerization initiator 1-hydroxycyclohexyl phenyl ketone was added in an amount corresponding to 5 mass % (600 mg) and was dissolved uniformly. A monomer composition (polymerizable composition) was thus prepared. Incidentally, NTTA used here had been purified after the reaction by column chromatography, and the purity thereof was >99%.

The monomer composition obtained was cured by the following methods to give cured products.

Curing method (1): A 1 mm thick glass plate, a 100 μm PET film, and a 0.5 mm thick silicon mold having a 50 mm×50 mm hollow were stacked in this order, and the monomer composition was poured into the silicon mold. Further, a PET film and a glass plate were stacked thereon, and the unit was fixed. Thereafter, the composition was cured by the application of 360 nm wavelength UV light.

Curing method (2): With a bar coater, the composition was spread on substrates so that the film thickness would be 23 μM or 50 μm. A PET film was laminated thereon, and the composition was cured by the application of 360 nm wavelength UV light.

The cured plate obtained by the curing method (1) was tested to determine the specific gravity of the cured product. The cured films obtained by the curing method (2) were tested to determine the pencil hardness, the curling properties and the adhesion. The curing shrinkage was 10.5%. The cured product with a film thickness of 23 μm showed curling properties of 20.1 mm, an adhesion of 100/100, and a pencil hardness of 3H. The evaluation results are described in Table 1.

Example 4 and Comparative Examples 1 and 2

Monomer compositions were prepared in the same manner as in Example 3 by adding 5 mass % of polymerization initiator 1-hydroxycyclohexyl phenyl ketone to each of NTTM produced in Example 2, trimethylolpropane triacrylate (TMPTA) and trimethylolpropane trimethacrylate (TMPTM). Cured products of the compositions were fabricated in the same manner, and the properties were measured. The evaluation results are described in Table 1.

TABLE 1

|  | Example 3 | Comparative Example 1 | Example 4 | Comparative Example 2 |
| --- | --- | --- | --- | --- |
| Triacrylate or trimethacrylate | NTTA | TMPTA | NTTM | TMPTM |
| Curing shrinkage (%) | 10.5 | 14.1 | 9.6 | 10.5 |
| Curling properties (mm) | 20.1 | 34.5 | 11.0 | >35.0 |
| Adhesion | 100/100 | 100/100 | 100/100 | 100/100 |
| Pencil hardness | 3H | 3H | 3H | 3H |

As shown in Table 1, the triacrylate of the present invention gave cured products which exhibited good and balanced properties in all the evaluation items consisting of curing shrinkage, curling properties, adhesion and pencil hardness. While the trimethacrylate of Comparative Example 2 had a large curing shrinkage and poor curling properties, the trimethacrylate of the present invention attained a small curing shrinkage and low curling properties.

In Examples 5 and 6 and Comparative Examples 3 and 4 below, polymerizable compositions were prepared which included the triacrylate monomer or the trimethacrylate monomer synthesized in Example 1 or 2, and a urethane acrylate oligomer generally used in applications such as building materials (trade name "SHIKOH UV-7510B" manufactured by The Nippon Synthetic Chemical Industry Co., Ltd., pencil hardness B). The compositions were cured, and the properties of the cured products were evaluated. Separately, cured products were prepared in the same manner except that TMPTA and TMPTM were used, and their properties were evaluated.

Flex Resistance:

In accordance with JIS K 5600-5-1, a cured thin plate with a thickness of 50 μm formed on a 0.5 mm thick polycarbonate as a substrate material was bent 180° by the use of a cylindrical mandrel bend tester manufactured by COTEC. The cured film was visually inspected for cracks or separation. The evaluation results indicate the maximum diameter of the mandrel which caused cracks or separation.

Example 5

On a 45° C. water bath, 4.5 g of NTTA produced in Example 1 and 4.5 g of the urethane acrylate oligomer were stirred together to give a uniform solution. To the solution, 450 mg of 1-hydroxycyclohexyl phenyl ketone was added and dissolved therein, thus preparing a polymerizable composition.

The polymerizable composition obtained was cured by the curing method (2) described in Example 3, and the properties of the cured products were measured. The pencil hardness was 21-1, the flex resistance was 10 mm, the curling properties of the 50 μm thick film were 7.5 mm, and the adhesion was 100/100. The evaluation results are described in Table 2.

Example 6 and Comparative Examples 3 and 4

NTTM produced in Example 2, TMPTA and TMPTM were each mixed together with the equal mass of the urethane acrylate oligomer, thus giving uniform solutions. Similarly to Example 5, polymerizable compositions were prepared by adding polymerization initiator 1-hydroxycyclohexyl phenyl ketone in an amount of 5 mass % relative to the total amount of resins. Cured products were fabricated in the same manner, and their properties were measured. The evaluation results are described in Table 2.

TABLE 2

|  | Example 5 | Comparative Example 3 | Example 6 | Comparative Example 4 |
|---|---|---|---|---|
| Triacrylate or trimethacrylate | NTTA | TMPTA | NTTM | TMPTM |
| Pencil hardness | 2H | 2H | H | 2H |
| Flex resistance (mm) | 10 | 20 | 13 | 20 |
| Curling properties (mm) | 7.5 | 20.1 | 5.0 | 13.3 |
| Adhesion | 100/100 | 100/100 | 100/100 | 100/100 |

The compositions discussed here contained a urethane acrylate oligomer which was characterized by its flexibility. As shown in Table 2, the cured products of Comparative Examples exhibited poor curling properties and poor flex resistance as compared to when the inventive triacrylate compound was used as a crosslinking agent. In contrast, the cured products of Examples 5 and 6 maintained the flexibility of the urethane acrylate oligomer, and exhibited smaller curls and good adhesion. Further, the inventive cured products attained practically sufficient pencil hardness.

INDUSTRIAL APPLICABILITY

As discussed above, the triacrylate compounds represented by the formula (1) are characterized by their capability of giving cured products excellently balanced in properties such as low curing shrinkage, low curling properties, good adhesion and surface hardness.

Further, the triacrylate compounds represented by the formula (1) may be used in the form of various curable resin compositions, and such compositions give cured products which are excellently balanced in properties such as low curing shrinkage, high flex resistance, adhesion and low curling properties.

The triacrylate compounds of the invention represented by the formula (1), and compositions including the compounds, which attain the characteristics described above, may be used in various applications such as, for example, crosslinking agents, inks, paints, coating agents, hard coats, films, adhesives, pressure sensitive adhesives, surface processing agents, lenses, resists, polarizers, sealants, liquid crystals, dental materials and nail cosmetics.

The entire contents of Japanese Patent Application No. 2014-215803 (filed: Oct. 22, 2014) are incorporated herein by reference. All publications, patent applications and technical standards mentioned in the present specification are herein incorporated by reference to the same extent as if each individual publication, patent application or technical standard was specifically and individually indicated to be incorporated by reference.

The invention claimed is:

1. A triacrylate compound represented by formula (1):

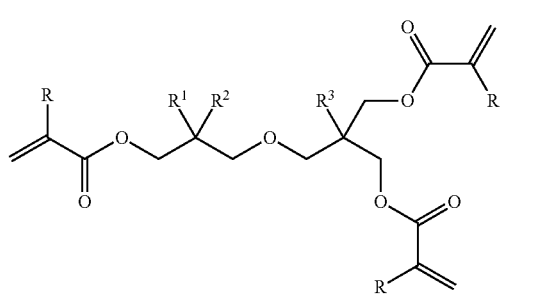

wherein each R is independently a hydrogen atom, an alkyl group having 1 to 6 carbon atoms or a halogen atom, $R^1$ and $R^2$ are each independently a linear or branched alkyl group having 1 to 6 carbon atoms, and $R^3$ is a linear or branched alkyl group having 1 to 6 carbon atoms or a hydroxymethyl group.

2. A composition comprising the triacrylate compound of claim 1, and a radical polymerization initiator.

3. The composition of claim 2, wherein the radical polymerization initiator is a radical photopolymerization initiator.

4. The composition of claim 2, further comprising at least one member selected from the group consisting of a polymerizable monomer other than the triacrylate compound, and a polymerizable oligomer.

5. The composition of claim 4, comprising at least one polymerizable oligomer selected from the group consisting of a urethane acrylate oligomer and a urethane methacrylate oligomer.

6. A polymer comprising a structural unit represented by formula (5):

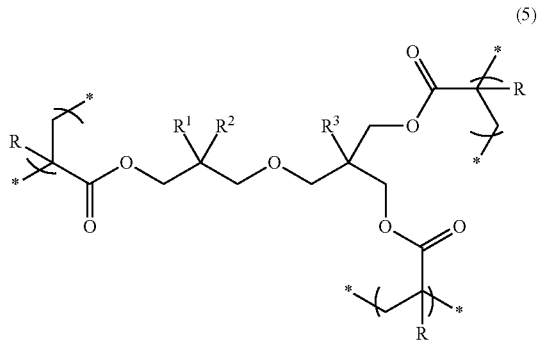

wherein $R^1$ and $R^2$ are each independently a linear or branched alkyl group having 1 to 6 carbon atoms, $R^3$ is a linear or branched alkyl group having 1 to 6 carbon atoms or a hydroxymethyl group, each R is independently a hydrogen atom, an alkyl group having 1 to 6 carbon atoms or a halogen atom, and each * indicates a binding site of the structural unit in the polymer.

7. A cured product of the composition of claim 2.
8. An ink comprising the composition of claim 2.
9. A coating agent comprising the composition of claim 2.
10. A film comprising a cured product of the composition of claim 2.

11. An adhesive comprising the composition of claim 2.

12. A method for producing a triacrylate compound represented by the formula (1), comprising subjecting a polyol compound represented by formula (2) to a dehydration condensation reaction with an unsaturated carboxylic acid compound represented by formula (3a),

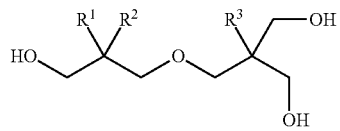
(2)

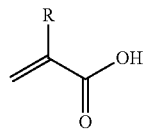
(3a)

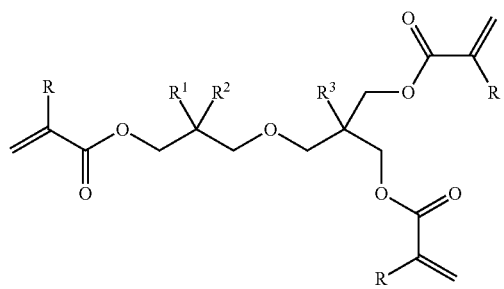
(1)

wherein each R is independently a hydrogen atom, an alkyl group having 1 to 6 carbon atoms or a halogen atom, $R^1$ and $R^2$ are each independently a linear or branched alkyl group having 1 to 6 carbon atoms, and $R^3$ is a linear or branched alkyl group having 1 to 6 carbon atoms or a hydroxymethyl group.

13. A method for producing a triacrylate compound represented by formula (1), comprising subjecting a polyol compound represented by formula (2) to a transesterification reaction with an unsaturated carboxylate ester compound represented by formula (3b),

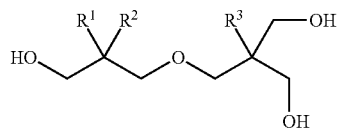
(2)

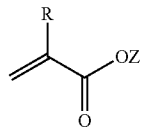
(3b)

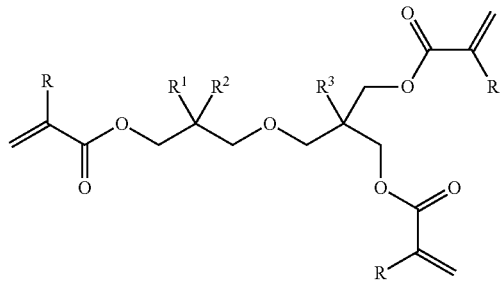
(1)

wherein each R is independently a hydrogen atom, an alkyl group having 1 to 6 carbon atoms or a halogen atom, $R^1$ and $R^2$ are each independently a linear or branched alkyl group having 1 to 6 carbon atoms, $R^3$ is a linear or branched alkyl group having 1 to 6 carbon atoms or a hydroxymethyl group, and Z is an alkyl group having 1 to 6 carbon atoms).

14. The triacrylate compound of claim 1, wherein each R is independently the hydrogen atom or the alkyl group having 1 to 3carbon atoms.

15. The triacrylate compound of claim 1, wherein each R is independently the hydrogen atom or a methyl group.

16. The triacrylate compound of claim 1, wherein $R^1$ and $R^2$ are each independently a linear alkyl group having 1 to 4 carbon atoms.

17. The triacrylate compound of claim 1, wherein $R^1$ and $R^2$ are each independently a methyl group.

18. The triacrylate compound of claim 1, wherein $R^3$ is a linear alkyl group having 1 to 6 carbon atoms.

19. The triacrylate compound of claim 1, wherein $R^3$ is a linear alkyl group having 1 or 2 carbon atoms.

20. The triacrylate compound of claim 1, wherein each R is a hydrogen atom or a methyl group, $R^1$ and $R^2$ are each a methyl group, and $R^3$ is an alkyl group having 1 to 2 carbon atoms.

* * * * *